(12) United States Patent
Mattes

(10) Patent No.: US 6,177,520 B1
(45) Date of Patent: Jan. 23, 2001

(54) ORGANIC COMPOUNDS

(75) Inventor: Henri Mattes, Brunstatt (FR)

(73) Assignee: Novartis AG, Basel (CH)

( * ) Notice: Under 35 U.S.C. 154(b), the term of this patent shall be extended for 0 days.

(21) Appl. No.: 08/984,640

(22) Filed: Dec. 3, 1997

(30) Foreign Application Priority Data

Dec. 4, 1996 (GB) .................................................. 9625166

(51) Int. Cl.$^7$ ....................................................... C08F 8/00
(52) U.S. Cl. .................... 525/333.3; 525/333.4; 525/333.6; 525/383; 525/386
(58) Field of Search ................. 525/383, 333.3, 525/333.4, 333.6, 386

(56) References Cited

U.S. PATENT DOCUMENTS

| | | | | |
|---|---|---|---|---|
| 5,242,974 | * | 9/1993 | Holmes | 525/54.11 |
| 5,550,215 | * | 8/1996 | Holmes | 525/54.11 |

* cited by examiner

Primary Examiner—Bernard Lipman
(74) Attorney, Agent, or Firm—David E. Wildman; Gregory D. Ferraro

(57) ABSTRACT

Use of a compound of formula I

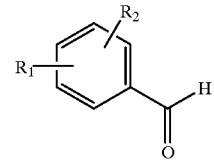

wherein
$R_1$ is a $C_{1-4}$ alkoxy or thioalkoxy group, and
$R_2$ is a group of formula $SR_{10}$ or $OR_{10}$
   wherein $R_{10}$ is a $C_{1-4}$ carboxylic or thiocarboxylic acid residue in salt, ester, free acid or activated form,
or an activated form thereof,
as a linker in solid phase synthesis of organic compounds, preferably of carbamates and secondary amines, and in addition are provided processes, solid phase systems and intermediates based on the compound of formula I.

3 Claims, No Drawings

ORGANIC COMPOUNDS

This invention relates to benzaldehyde derivatives and in particular to use of such derivatives as linkers for solid phase synthesis of secondary amines and disubstituted carbamates.

Accordingly the present invention provides the use of a compound of formula I

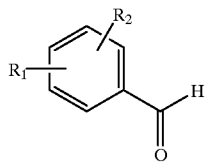

I wherein
$R_1$ is a $C_{1-4}$ alkoxy or thioalkoxy group, and
$R_2$ is a group of formula $SR_{10}$ or $OR_{10}$
wherein $R_{10}$ is a $C_{1-4}$ carboxylic or thiocarboxylic acid residue in salt, ester, free acid or activated form,
or an activated form thereof,
as a linker in solid phase synthesis of organic compounds.

In the use of the invention the symbols of formula I have the following preferred meanings.

Preferably $R_1$ is a $C_{1-4}$ alkoxy group, most preferably a methoxy group.

Preferably $R_2$ is a group of formula $OR_{10}$.

Preferably $R_{10}$ is a $C_2$ carboxylic acid residue. Preferably $R_{10}$ is in free acid or activated form, e.g. as an acid halide or anhydride. Most preferably $R_{10}$ is a group of formula —$CH_2$—COOH or an activated form thereof.

Preferred compounds for use in the invention are compounds of formula II

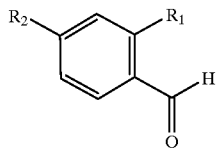

II especially compounds having the preferred significances for $R_1$ and $R_2$ given above.

A particularly preferred compound for use in the invention is the compound of formula IX

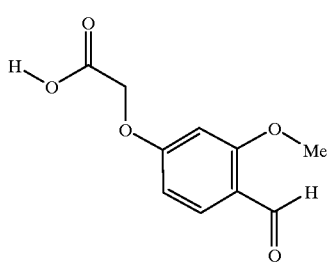

IX or an activated form thereof. The particularly preferred compound of formula IX is commercially available.

The compounds of formula I are useful as linkers for solid phase synthesis. Compounds of formula I when attached to a solid phase provide novel solid phase systems.

Thus in a further aspect the invention provides a solid phase system of formula III

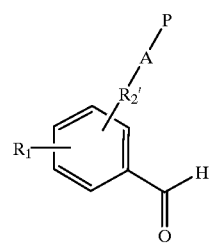

III wherein
$R_1$ is as defined above;
$R_2'$ is the diradical of $R_2$ as defined above;
A is a spacer selected from the group consisting of $C_{1-4}$ alkyl, —NH—, —NR— (urethane), —O— (ether) and
P is a solid phase carrier material,
or an activated form thereof.

In particular the invention provides a solid phase system of formula IV

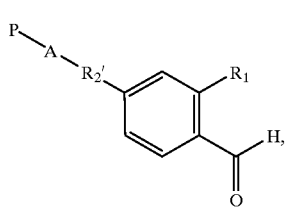

IV or especially a solid phase system of formula IVa

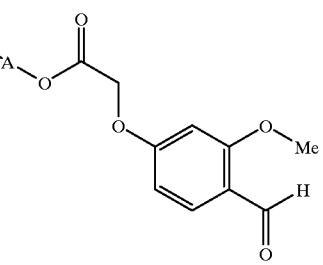

IVa wherein the symbols are as defined above, or activated forms thereof.

Any suitable solid phase carrier material may be used in the present invention, including those known and used in the solid phase synthesis art. For example, the solid phase may be a naturally occurring or synthetic organic or inorganic polymer in particulate form, e.g. as beads, or preferably as a surface coating or layer on a suitable inert substrate material. Examples of suitable polymer materials include crosslinked polystyrene or a graft copolymer of polyethylene glycol on polystyrene, e.g. polystyrene pins, Gly-HMD-MA/DMA pins and HEMA pins. Conveniently the polymer comprises surface amino groups, e.g. amino methyl groups, to facilitate attachment of the compound of formula I.

The solid phase systems of formulae III, IV and IVa are prepared by coupling a corresponding compound of formulae I, II or IX, or an activated form thereof, with a solid phase. Such processes are included within the scope of the invention.

The compounds of formula I and the solid phase systems of formula III are particularly useful for the solid phase preparation of secondary amines and disubstituted carbamates. Conveniently the present invention involves the synthesis of a secondary amine intermediate of formula V

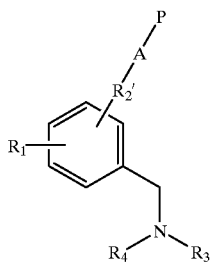

especially an intermediate of formula Va

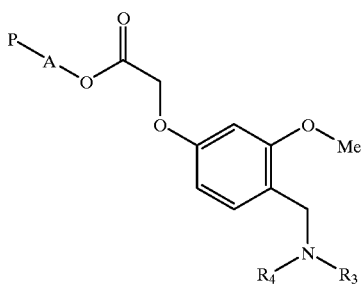

wherein $R_1$, $R_2'$, A and P are as defined above, $R_3$ and $R_4$ which may be the same or different are organic chemical residues, e.g. residues selected to provide desired biological activities in the resultant secondary amine and carbamate products.

For example, $R_3$ and $R_4$ which may be the same or different are is —$R_5$, —$R_5C(O)R_6$, —$R_5C(O)OR_6$, —$R_5OC(O)R_6$, —$R_5OC(O)OR_6$, —$R_5NR_6C(O)R_7$, —$R_5C(O)NR_6R_7$, —$R_5OC(O)NR_6R_7$, —$R_5NR_6C(O)NR_7R_8$, —$R_5NR_6C(O)OR_7$, —$R_5$—O—$R_6$, —$R_5$—$NR_6R_7$, —$R_5$—S—$R_6$, —$R_5$—$SO_m$—$R_6$, —$R_5OR_6$—O—$R_7$, —$R_5NR_6R_7$—O—$R_8$, —$R_5SO_mR_6$—O—$R_7$, —$R_5C(O)R_6$—O—$R_7$, —$R_5C(O)OR_6$—O—$R_7$, —$R_5OC(O)R_6$—O—$R_7$, —$R_5OC(O)OR_6$—O—$R_7$, —$R_5NR_6C(O)R_7$—O—$R_8$, —$R_5C(O)NR_6R_7$—O—$R_8$, —$R_5OC(O)NR_6R_7$—O—$R_8$, —$R_5NR_6C(O)NR_7R_8$—O—$R_9$, —$R_5NR_6C(O)OR_7$—O—$R_8$, —$R_5OR_6$—S—$R_7$, —$R_5NR_6R_7$—S—$R_8$, —$R_5SO_mR_6$—S—$R_7$, —$R_5C(O)R_6$—S—$R_7$, —$R_5C(O)OR_6$—S—$R_7$, —$R_5OC(O)R_6$—S—$R_7$, —$R_5OC(O)OR_6$—S—$R_7$, —$R_5NR_6C(O)R_7$—S—$R_8$, —$R_5C(O)NR_6R_7$—S—$R_8$, —$R_5OC(O)NR_6R_7$—S—$R_8$, —$R_5NR_6C(O)NR_7R_8$—S—$R_9$, —$R_5NR_6C(O)OR_7$—S—$R_8$, —$R_5OR_6$—$NR_7R_8$, —$R_5NR_6R_7$—$NR_8R_9$, —$R_5SO_mR_6$—$NR_7R_8$, —$R_5C(O)R_6$—$NR_7R_8$, —$R_5C(O)OR_6$—$NR_7R_8$, —$R_5OC(O)R_6$—$NR_7R_8$, —$R_5OC(O)OR_6$—$NR_7R_8$, —$R_5NR_6C(O)R_7$—$NR_8R_9$, —$R_5C(O)NR_6R_7$—$NR_8R_9$, —$R_5OC(O)NR_6R_7$—$NR_8R_9$, —$R_5NR_6C(O)NR_7R_8$—$NHR_9$ or —$R_5NR_6C(O)OR_7$—$NR_8R_9$, where $R_5$, $R_6$, $R_7$, $R_8$ and $R_9$ are each independently $C_{1-10}$alkyl, $C_{1-10}$alkenyl, $C_{1-10}$alkynyl, $C_{6-10}$aryl, $C_{6-14}$aralkyl, $C_{6-14}$aralkenyl or $C_{6-14}$aralkynyl and m is 1,2,3 or 4; and where $R_5$, $R_6$, $R_7$, $R_8$ and $R_9$ are each unsubstituted or substituted with up to 6 substituents selected from halo, $NO_2$, —OH, $C_{1-4}$alkyl, —SH, —$SO_3$, —$NH_2$, $C_{1-4}$acyl, $C_{1-4}$acyloxy, $C_{1-4}$alkylamino, $C_{1-4}$dialkylamino, trihalomethyl, —CN, $C_{1-4}$alkylthio, $C_{1-4}$alkylsulfinyl, or $C_{1-4}$alkylsufonyl, provided that all the R substituents are not identical, or each $R_3$ or $R_4$ alone or together forms a cyclic structure, e.g. a carbocyclic or heterocyclic ring. Preferred examples for such a carbocyclic ring are $C_5$–$C_8$ carbocyclic rings. Preferred examples for such a heterocyclic ring are pyrrole, imidazole, benzimidazole, pyrazole, pyridine, pyrazine, pyrimidine, pyridazine, triazine, indolizine, isoindole, indole, indazole, purine, isoquinoline, quinoline, phtalazine, quinoxaline, benzodiazine, quinazoline, pteridine, carbazole, beta-carboline, thiophene, benzothiophene, furan, benzofuran, triazole, isoxazole, oxazole, thiazole, isothiazole, pyrone, indoxazine or benzopyrone. Such cyclic structures can be unsubstituted or substituted by at least one residue selected from the group consisting of halo, $NO_2$, —OH, $C_{1-4}$alkyl, —SH, —$SO_3$, —$NH_2$, $C_{1-4}$acyl, $C_{1-4}$acyloxy, $C_{1-4}$alkylamino, $C_{1-4}$dialkylamino, trihalomethyl, —CN, $C_{1-4}$alkylthio, $C_{1-4}$alkylsulfinyl and $C_{1-4}$alkylsulfonyl.

The intermediates of formula V may be prepared from the solid phase systems of formulae III by processes involving reductive amination with a primary amine followed by a second reductive amination with an aldehyde or ketone.

Thus in a further aspect the invention provides a process for the preparation of an intermediate of formula V comprising reacting a solid phase system of formula III with a primary amine, e.g. in the presence of sodium cyanoborohydride, dissolved e.g. in DMF/AcOH 97:3, or in the presence of titanium tetraisopropoxide and sodium cyanoborohydride, dissolved e.g. in dichloromethane, followed by a reaction with an aldehyde or ketone, e.g. in the presence of sodium cyanoborohydride, dissolved e.g. in DMF/AcOH 97:3, or in the presence of titanium tetraisopropoxide and sodium cyanoborohydride, dissolved e.g. in dichloromethane.

The intermediates of formula V may be used to prepare corresponding carbamates and secondary amines by appropriate cleavage of the —$NR_3R_4$ group from the intermediate with a suitable cleavage reagent followed by further processing as required.

Thus for example, carbamates may be prepared from the intermediates of formula V by treatment with a corresponding activated carbonate, such as a halocarbonate, e.g. a chlorocarbonate, e.g. a compound of formula VI

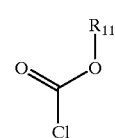

wherein $R_{11}$ is a functional group which does not react with a chlorocarbonate, wherein $R_{11}$ preferably is as defined as residues $R_3$ or $R_4$ of compunds of formulae V or Va, above, inclusive the respective preferences, to yield a carbamate, e.g. of formula VII

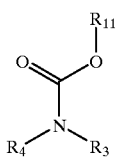

VII wherein the symbols $R_3$, $R_4$ and $R_{11}$ are as defined above.

Thus also for example, secondary amines may be prepared from the intermediates of formula V by a two step process involving i) a first step in which the intermediate is treated with an appropriate activated carbonate such as a haloethylhalocarbonate, e.g. α-chloroethylchlorocarbonate

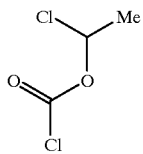

to yield a carbamate intermediate, e.g. of formula VIII

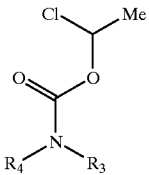

VIII wherein $R_3$ and $R_4$ are as defined for the compounds of formula V, above; and ii) a second step in which the carbamate intermediate, e.g. the compound of formula VIII is cleaved, e.g. by treatment with an appropriate agent such as an alcohol, e.g. methanol, to yield the corresponding secondary amine of formula

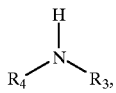

wherein $R_3$ and $R_4$ are as defined above.

Such processes for the preparation of carbamates and secondary amines, including the first and second steps separately of the secondary amine process as well as the carbamate intermediates per se, are further aspects of, and are included within the scope of, the present invention.

The invention is further described by way of illustration only in the following non-limiting examples.

EXAMPLES

Example 1

Attachment of Compound of Formula IX to Solid Phase

Aminomethyl polystyrene pins (Chiron mimotopes) are treated for 72 hours at room temperature with a solution containing 0.15M IX (commercially available from Bachem AG), 0.15M HATU and 0.2M N-methyl morpholine in DMF. The pins are washed extensively with DMF, MeOH and DCM.

Examples 2.1 and 2.2

Preparation of Immobilised Intermediate with —$NR_3R_4$ Substituent 2.1 To the pins prepared as above is added a solution containing 0.3M isobutylamine and 0.1M $NaBH_3CN$ in DMF/AcOH 97:3. The reaction mixture is left at room temperature for 24 hours and subsequently washed with DMF/AcOH, MeOH, DMF and DCM. A solution containing 0.3M cyclohexylcarboxaldehyde and 0.1M $NaBH_3CN$ in DMF/AcOH 97:3 is then added to the pins. The reaction is left at room temperature for 48 hours and subsequently washed with DMF/AcOH, MeOH, DMF, 0.1 M LiOH in Dioxane/Water 7:3, DMF and DCM.

2.2 To the pins prepared as above is added a solution containing 0.2M isobutylamine and 0.2M $Ti(Oi-Pr)_4$ in $CH_2Cl_2$. After 18 hours at room temperature $NaBH_3CN$ is added in order to reach a 0.1 M concentration and the reaction mixture is left at room temperature for 30 hours. The pins are subsequently washed with DMF/MeOH 9:1, DMF/$Et_3N$ 7:3, DMSO, MeOH and DCM. A solution containing 0.3M cyclohexylcarboxaldehyde and 0.3M $Ti(Oi-Pr)_4$ in $CH_2Cl_2$ is then added to the pins. After 18 hours at room temperature $NaBH_3CN$ is added in order to reach a 0.1M concentration and the reaction mixture is left at room temperature for 30 hours. The pins are subsequently washed with DMF/MeOH 9:1, MeOH, DMSO, 0.1M LiOH in Dioxane/Water 7:3, DMF and DCM.

Example 3

Preparation of Carbamate

The pins prepared in Example 2 are treated with a 0.2M solution of phenlychlorocarbonate previously filtered through a $K_2CO_3$ plug, for 5 h at room temperature to yield the carbamate in solution as a crude product. This crude solution is treated with aminomethylpolystyrene for 2h and the solid material is filtered off. The crude product is characterised by HPLC (C-18RP, Waters, gradient 10–80% acetonitrile with water containing 0–1% TFA over 20 min, 1.0 ml/min flow rate, detection at 21 5 nm) and by ESMS.

Example: cyclohexylmethyl-isobutyl-carbamic acid phenyl ester C18 H27 N O2 M+ 289.4 %RA: 100, %RIC: 80.3

Other carbamates are produced analogously using corresponding chlorocarbonate and immobilised solid phase intermediate starting materials.

Example 4

Preparation of Chlorocarbamate Intermediate

Pins prepared according to Examples 2.1 or 2.2, however, using (2-morpholino-4yl-ethyl)amine and cyclohexylcarboxaldehyde, are treated for 8 h at room temperature with a 0.2M solution of alpha chloroethylchlorocarbonate, previously filtered through a plug of solid $K_2CO_3$, to give a solution of the crude carbamate product. If desired this crude product is further processed/purified as described in Example 3.

Example 5

Preparation of Secondary Amine

The crude carbamate solution as obtained in Example 4 is treated with MeOH for 5 h at 60° C. to give the crude amine hydrochloride, after evaporation of the solvent. This crude product is characterised by HPLC (C-18RP, Waters, gradient 10–80% acetonitrile with water containing 0–1% TFA over 20 min, 1.0 ml/min flow rate, detection at 215 nm) and by ESMS.

Example: cyclohexylmethyl-(2-morpholin-4yl-ethyl)-amine hydrochloride C13H26N2O.HCl MH+ 227.0 %RA: 100, %RIC: 90.17

Other secondary amines are produced analogously using corresponding chlorocarbonate and solid phase intermediate starting materials.

What is claimed is:

1. A solid phase system for the synthesis of organic compounds comprising a compound of formula III

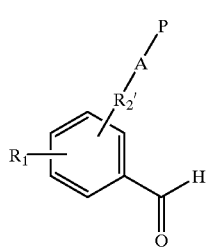

III wherein $R_1$ is a $C_{1-4}$ alkoxy or thioalkoxy group, $R_2'$ is a diradical of a group of formula $SR_{10}$ or $OR_{10}$ wherein $R_{10}$ is a $C_{1-4}$ carboxylic or thiocarboxylic acid residue in salt, ester, free acid or activated form, A is a spacer selected from the group consisting of $C_{1-4}$ alkyl, —NH—, —NR— (urethane), —O— (ester), and P is a solid phase carrier material, or an activated form thereof.

2. A solid phase system for the synthesis of organic compounds comprising a compound of formula IV

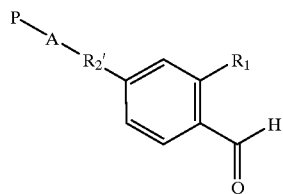

IV wherein $R_1$ is a $C_{1-4}$ alkoxy or thioalkoxy group, $R_2'$ is a diradical of a group of formula $SR_{10}$ or $OR_{10}$ wherein $R_{10}$ is a $C_{1-4}$ carboxylic or thiocarboxylic acid residue in salt, ester, free acid or activated form, A is a spacer selected from the group consisting of $C_{1-4}$ alkyl, —NH—, —NR— (urethane), —O— (ester), and P is a solid phase carrier material, or an activated form thereof.

3. A solid phase system for the synthesis of organic compounds comprising a compound of formula IVa

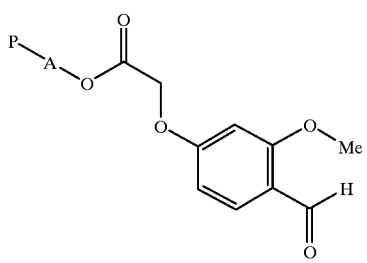

IVa wherein

A is a spacer selected from the group consisting of $C_{1-4}$ alkyl, —NH—, —NR— (urethane), —O— (ester), Me is methyl, and P is a solid phase carrier material, or an activated form thereof.

* * * * *